(12) United States Patent  
Davis et al.

(10) Patent No.: US 8,153,844 B2
(45) Date of Patent: Apr. 10, 2012

(54) PROCESS FOR MAKING 3-SUBSTITUTED 2-AMINO-5-HALOBENZAMIDES

(75) Inventors: Richard F. Davis, Bear, DE (US); Rafael Shapiro, Wilmington, DE (US); Eric G. Taylor, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 637 days.

(21) Appl. No.: 12/373,651

(22) PCT Filed: Jun. 27, 2007

(86) PCT No.: PCT/US2007/014972
§ 371 (c)(1),
(2), (4) Date: Jan. 13, 2009

(87) PCT Pub. No.: WO2008/010897
PCT Pub. Date: Jan. 24, 2008

(65) Prior Publication Data
US 2009/0306372 A1    Dec. 10, 2009

Related U.S. Application Data

(60) Provisional application No. 60/831,781, filed on Jul. 19, 2006.

(51) Int. Cl.
C07C 231/02 (2006.01)
C07C 271/28 (2006.01)
C07D 265/26 (2006.01)

(52) U.S. Cl. .......... 564/163; 564/133; 564/168; 560/30; 560/31; 544/94

(58) Field of Classification Search .................. None
See application file for complete search history.

(56) References Cited

U.S. PATENT DOCUMENTS

| | | | |
|---|---|---|---|
| 3,515,744 A | 6/1970 | Steinbrunn et al. | |
| 4,265,832 A | 5/1981 | Krebs et al. | |
| 4,316,020 A | 2/1982 | Reissenweber | |
| 4,873,232 A | 10/1989 | Krantz et al. | |

FOREIGN PATENT DOCUMENTS

| | | |
|---|---|---|
| DE | 939151 C | 2/1956 |
| DE | 2925175 A1 | 1/1981 |
| EP | 315138 B1 | 1/1993 |
| WO | 03015518 A1 | 2/2003 |
| WO | 2006055922 A2 | 5/2006 |
| WO | 2006062978 A1 | 6/2006 |
| WO | 2006065479 A2 | 6/2006 |

OTHER PUBLICATIONS

D. Ben-Ishai and E. Katchalski, J. Am. Chem. Soc., 1952, vol. 74, pp. 3688-3689.
A. H. F. Lee and E. T. Kool, J. Org. Chem., 2005, vol. 70, pp. 132-140.
Gary Coppola, The Chemistry of Isatoic Anhydride, Synthesis, 1980, vol. 7, pp. 505-536.
XP002464992 Chemical Abstracts CHEMCATS Database, "Rare Chemicals Catalogue", Aug. 21, 2006, Rare Chemicals GMBH, Kiel, Germany.
XP002464993 Chemical Abstracts CHEMCATS Database, "Oakwood Products Catalog", Jul. 16, 2007, Oakwood Products, Inc., West Columbia, SC, 29172 USA.

Primary Examiner — Brian J Davis
(74) Attorney, Agent, or Firm — Roman Kucharczyk

(57) ABSTRACT

Disclosed is a method for preparing a compound of Formula 1 by contacting compound of Formula 2 with $R^1$—$NH_2$ in the presence of a carboxylic acid and a method for preparing a compound of Formula 2 by contacting a compound of Formula 4 with phosphorus tribromide.

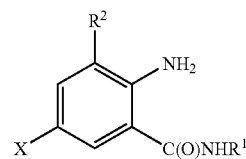

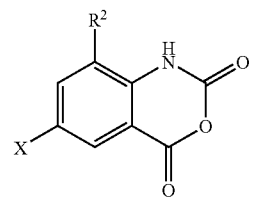

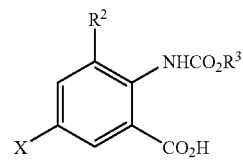

wherein $R^1$ is H, $C_1$-$C_4$ alkyl, cyclopropyl, cyclopropylmethyl or methylcyclopropyl; $R^2$ is $CH_3$ or Cl; $R^3$ is $C_1$-$C_6$ alkyl or $C_3$-$C_6$ alkenyl, each optionally substituted with up to 3 halogen and up to 1 phenyl; and X is Cl or Br.
Also disclosed is a method for preparing a compound of Formula 5

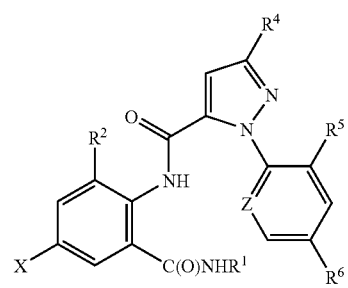

wherein $R^4$, $R^5$, $R^6$ and Z are as defined in the disclosure, using a compound of Formula 1 that is characterized by preparing the compound of Formula 1 by the method above.

10 Claims, No Drawings

PROCESS FOR MAKING 3-SUBSTITUTED 2-AMINO-5-HALOBENZAMIDES

BACKGROUND OF THE INVENTION

As is disclosed in PCT Patent Publications WO 2003/015518, WO 2006/055922 and WO 2006/062978, 3-substituted 2-amino-5-halobenzamides are useful starting materials for preparing arthropodicidal diamides of anthranilic acid. WO 2006/062978 discloses that 3-substituted 2-amino-5-halobenzamides can be prepared by halogenation of corresponding 3-substituted 2-aminobenzamides. As the amino group is strongly activating for electrophilic substitution on the benzene ring, 3-substituted 2-aminobenzamides react rapidly with electrophilic halogenating reagents at the 5-position. However, the resulting products, being anilines themselves and only partially deactivated by monohalogenation, are susceptible to further halogenation. Accordingly there is a need for new methods to prepare 3-substituted 2-amino-5-halobenzamides without reacting an aniline directly with a halogenating agent.

SUMMARY OF THE INVENTION

This invention provides a method for preparing a compound of Formula 1

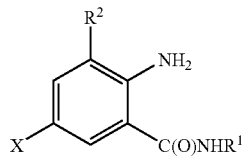

1 wherein $R^1$ is H, $C_1$-$C_4$ alkyl, cyclopropyl, cyclopropylmethyl or methylcyclopropyl;
$R^2$ is $CH_3$ or Cl; and
X is Cl or Br;
comprising contacting a compound of Formula 2

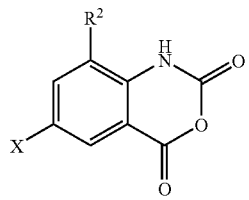

2 with a compound of Formula 3

$R^1$—$NH_2$    3 in the presence of a carboxylic acid.

This invention also provides a method for preparing the compound of Formula 2 wherein $R^2$ is $CH_3$ or Cl; and X is Cl or Br; comprising contacting a compound of Formula 4

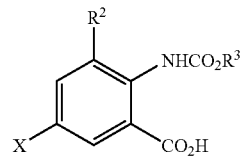

4 wherein $R^3$ is $C_1$-$C_6$ alkyl or $C_3$-$C_6$ alkenyl, each optionally substituted with up to 3 halogen and up to 1 phenyl;
with phosphorus tribromide.

This invention further relates to a novel compound of Formula 4 wherein $R^2$ is $CH_3$ or Cl; $R^3$ is $C_1$-$C_6$ alkyl or $C_3$-$C_6$ alkenyl, each optionally substituted with up to 3 halogen and up to 1 phenyl; and X is Cl or Br; provided that when $R^2$ and X are each Cl, then $R^3$ is other than $CH_3$; which is a useful intermediate for preparing compounds of Formulae 1 and 2 by the aforedescribed methods.

This invention also relates to a method for preparing a compound of Formula 5

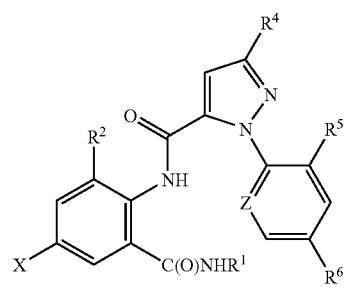

5 wherein
X is Cl or Br;
Z is $CR^7$ or N;
$R^1$ is H, $C_1$-$C_4$ alkyl, cyclopropyl, cyclopropylmethyl or methylcyclopropyl;
$R^2$ is $CH_3$ or Cl;
$R^4$ is Cl, Br, $CF_3$, $OCF_2H$ or $OCH_2CF_3$;
$R^5$ is F, Cl or Br;
$R^6$ is H, F or Cl; and
$R^7$ is H, F, Cl or Br;
using a compound of Formula 1. This method is characterized by preparing the compound of Formula 1 from the compounds of Formulae 2 and 3 by the method indicated above.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "optionally substituted" in the definition of a radical (e.g., alkyl or alkenyl) means that the radical is unsubstituted or is substituted with one or more substituents up to any stated limit of number of substituents. As "optionally substituted" includes the option of no substitution, the phrase "each optionally substituted with 1-3 substituents" means that optionally 0, 1, 2 or 3 substituents are present. Therefore "each optionally substituted with 1-3 substituents" is synonymous with "each optionally substituted with 0-3 substituents" and with "each optionally substituted with up to 3 substituents". Related phrases reciting "optionally substituted" are defined analogously. As further examples, "each optionally substituted with up to 3 halogen" is synonymous with "each optionally substituted with 1-3 halogen", and "each optionally substituted with up to 1 phenyl" is synonymous with "each optionally substituted with 0-1 phenyl". When "halogen" is recited in the context of a range that includes 1 or more than one (e.g., "up to 3 halogen"), the singular word form "halogen" means "halogens" or "halogen atoms" when more than one halogen atom is present. When more than one substituent is present, each substitution is independent of the other. For example, when two or more halogens are present as substituents, each of the halogen atoms can be the same or different halogens.

Ratios are generally recited herein as single numbers, which are relative to the number 1; for example, a ratio of 4 means 4:1.

As referred to in the present disclosure and claims, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid, and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

Embodiments of the present invention include:

Embodiment A1. The method described in the Summary of the Invention for preparing a compound of Formula 1 comprising contacting a compound of Formula 2 with a compound of Formula 3 in the presence of a carboxylic acid.

Embodiment A2. The method of Embodiment A1 wherein $R^1$ is $C_1$-$C_4$ alkyl, cyclopropyl, cyclopropylmethyl or methylcyclopropyl.

Embodiment A3. The method of Embodiment A2 wherein $R^1$ is $C_1$-$C_4$ alkyl or cyclopropylmethyl.

Embodiment A4. The method of Embodiment A3 wherein $R^1$ is methyl.

Embodiment A5. The method of Embodiment A1 wherein the mole ratio of the compound of Formula 3 to the compound of Formula 2 is from about 1.1 to about 2.

Embodiment A5a. The method of Embodiment A5 wherein the mole ratio of the compound of Formula 3 to the compound of Formula 2 is from about 1.1 to about 1.5.

Embodiment A5b. The method of Embodiment A5a wherein the mole ratio of the compound of Formula 3 to the compound of Formula 2 is from about 1.1 to about 1.3.

Embodiment A5c. The method of Embodiment A5b wherein the mole ratio of the compound of Formula 3 to compound of Formula 2 is from about 1.2 to about 1.3.

Embodiment A6. The method of Embodiment A1 wherein the compound of Formula 2 is contacted with the compound of Formula 3 in the presence of the carboxylic acid and in the presence of a suitable organic solvent.

Embodiment A7. The method of Embodiment A1 wherein the compound of Formula 2 is contacted with the compound of Formula 3 in the presence of the carboxylic acid in a reaction medium comprising a suitable organic solvent.

Embodiment A8. The method of Embodiment A7 wherein the reaction medium contains 5% water by weight or less.

Embodiment A9. The method of Embodiment A8 wherein the reaction medium contains 1% water by weight or less.

Embodiment A10. The method of Embodiment A9 wherein the reaction medium contains 0.1% water by weight or less.

Embodiment A11. The method of Embodiment A7 wherein the reaction medium is substantially anhydrous.

Embodiment A12. The method of any one of Embodiments A6 and A7 wherein the organic solvent comprises one or more solvents selected from esters, ketones, nitriles, haloalkanes, ethers, and halogenated and nonhalogenated aromatic hydrocarbons.

Embodiment A13. The method of Embodiment A12 wherein the organic solvent comprises a $C_2$-$C_3$ alkylcarboxylic acid ester of a $C_1$-$C_3$ alkanol.

Embodiment A14. The method of Embodiment A13 wherein the organic solvent comprises ethyl acetate.

Embodiment A15. The method of Embodiment A1 wherein the contact is in a reaction medium having a pH in a range of from about 3 to about 7

Embodiment A16. The method of Embodiment A15 wherein the carboxylic acid is selected to provide a pH within said range.

Embodiment A17. The method of Embodiment A1 wherein the carboxylic acid has an effective $pK_a$ between about 2 and about 5.

Embodiment A18. The method of Embodiment A1 wherein the carboxylic acid is $C_2$-$C_{18}$ alkylcarboxylic acid.

Embodiment A19. The method of Embodiment A18 wherein the carboxylic acid is acetic acid.

Embodiment A20. The method of Embodiment A1 wherein the mole ratio of the compound of Formula 3 to the carboxylic acid is from about 0.6 to about 3.

Embodiment A20a. The method of Embodiment A20 wherein the mole ratio of the compound of Formula 3 to the carboxylic acid is from about 0.6 to about 1.2.

Embodiment A20b. The method of Embodiment A20 wherein the mole ratio of the compound of Formula 3 to the carboxylic acid is from about 0.8 to about 3.

Embodiment A20c. The method of Embodiment A20b wherein the mole ratio of the compound of Formula 3 to the carboxylic acid is from about 0.8 to about 1.2.

Embodiment A21. The method of Embodiment A1 wherein the compound of Formula 2 is contacted with the compound of Formula 3 and the carboxylic acid at a temperature ranging between about 5 and about 75° C.

Embodiment A21a. The method of Embodiment A21 wherein the temperature is between about 15 and about 70° C.

Embodiment A21b. The method of Embodiment A21a wherein the temperatures is between about 35 and about 60° C.

Embodiment A21c. The method of Embodiment A21b wherein the temperature is between about 35 and about 55° C.

Embodiment A21d. The method of Embodiment A21b wherein the temperature is between about 50 and about 60° C.

Embodiment A22. The method of Embodiment A21d wherein the temperature is between about 50 and about 55° C.

Embodiment A23. The method of Embodiment A1 wherein the compound of Formula 3 is added to a mixture of the compound of Formula 2 and the carboxylic acid.

Embodiment A24. The method of Embodiment A23 wherein the compound of Formula 3 is added in anhydrous form (i.e. substantially anhydrous form).

Embodiment A25. The method of Embodiment A1 wherein the compound of Formula 2 is prepared by contacting a compound of Formula 4 with phosphorus tribromide.

Embodiment A26. The method of Embodiment A1 wherein the compound of Formula 3 is added to a mixture comprising the compound of Formula 2 and the carboxylic acid.

Embodiment B1. The method described in the Summary of the Invention for preparing a compound of Formula 2 comprising contacting a compound of Formula 4 with phosphorus tribromide.

Embodiment B4. The method of Embodiment B1 wherein $R^3$ is $C_1$-$C_4$ alkyl.

Embodiment B5. The method of Embodiment B4 wherein $R^3$ is unbranched at the carbon atom of $R^3$ bonded to oxygen.

Embodiment B6. The method of Embodiment B5 wherein $R^3$ is methyl or ethyl.

Embodiment B7. The method of Embodiment B1 wherein the compound of Formula 4 is contacted with the phosphorus tribromide in the presence of a suitable organic solvent.

Embodiment B8. The method of Embodiment B1 wherein the organic solvent comprise one or more solvents selected from esters, nitriles, hydrocarbons and halogenated hydrocarbons.

Embodiment B8a. The method of Embodiment B8 wherein the organic solvent comprises one or more solvents selected from esters, nitriles, haloalkanes, and halogenated and nonhalogenated aromatic hydrocarbons.

Embodiment B9. The method of Embodiment B8a wherein the organic solvent comprises one or more solvents selected from haloalkanes, and halogenated and nonhalogenated aromatic hydrocarbons.

Embodiment B10. The method of Embodiment B9 wherein the organic solvent comprises one or more solvents selected from 1,2-dichloroethane, benzene, toluene, xylene and chlorobenzene.

Embodiment B11. The method of Embodiment B10 wherein the organic solvent comprises toluene.

Embodiment B12. The method of Embodiment B1 wherein the mole ratio of the phosphorus tribromide to the compound of Formula 3 is from about 0.3 to about 3.

Embodiment B12a. The method of Embodiment B12 wherein the mole ratio of the phosphorus tribromide to the compound of Formula 3 is from about 0.3 to about 0.5.

Embodiment B13. The method of Embodiment B12a wherein the mole ratio of the phosphorus tribromide to the compound of Formula 3 is from about 0.33 to about 0.40.

Embodiment B14. The method of Embodiment B1 wherein the compound of Formula 3 is contacted with phosphorus tribromide at a temperature ranging between about 50 and about 90° C.

Embodiment B14a. The method of Embodiment B14 wherein the temperature ranges between about 50 and about 80° C.

Embodiment B14b. The method of Embodiment B15a wherein the temperatures ranges between about 60 to about 75° C.

Embodiment B15. The method of Embodiment B14b wherein the temperature ranges between about 60 and about 70° C.

Embodiment C1. The method of any one of Embodiments A1 and B1 wherein $R^2$ is methyl.

Embodiment C2. The method of any one of Embodiments A1 and B1 wherein X is Cl.

Embodiment C3. The method of any one of Embodiments A1 and B1 wherein X is Br.

Embodiment C4. The method of any one of Embodiments A1, A4 and B1 wherein $R^2$ is $CH_3$ and X is Cl.

Embodiment D1. A compound of Formula 4 wherein $R^2$ is $CH_3$ or Cl; $R^3$ is $C_1$-$C_6$ alkyl or $C_3$-$C_6$ alkenyl, each optionally substituted with up to 3 halogen and up to 1 phenyl; and X is Cl or Br; provided that when $R^2$ and X are each Cl, then $R^3$ is other than $CH_3$.

Embodiment D2. A compound of Embodiment D1 wherein $R^2$ is $CH_3$.

Embodiment D3. A compound of Embodiment D1 wherein $R^3$ is $C_1$-$C_4$ alkyl.

Embodiment D4. The compound of Embodiment D3 wherein $R^3$ is unbranched at the carbon atom of $R^3$ bonded to oxygen.

Embodiment D5. The compound of Embodiment D4 wherein $R^3$ is methyl or ethyl.

Embodiment D6. A compound of Embodiment D1 wherein X is Cl.

Embodiment D7. A compound of Embodiment D1 wherein X is Br.

Embodiment D8. A compound of Embodiment D1 wherein $R^2$ is $CH_3$ and X is Cl.

Embodiment D9. A compound of Embodiment D1 wherein $R^2$ is $CH_3$ and X is Br.

Embodiment D10. A compound of any one of Embodiments D1, D8 and D9 wherein $R^3$ is $C_1$-$C_2$ alkyl.

Embodiment D11. The compound of Embodiment D10 wherein $R^2$ is $CH_3$, $R^3$ is $CH_3$, and X is Cl.

Embodiment D12. The compound of Embodiment D10 wherein $R^2$ is $CH_3$, $R^3$ is $CH_3$, and X is Br.

Embodiment D13. The compound of Embodiment D10 wherein $R^2$ is $CH_3$, $R^3$ is $CH_2CH_3$, and X is Cl.

Embodiment D14. The compound of Embodiment D10 wherein $R^2$ is $CH_3$, $R^3$ is $CH_2CH_3$, and X is Br.

Embodiment D15. A compound of Embodiment D1 wherein when X is Cl, then $R^2$ is other than Cl.

Embodiment D16. A compound of Embodiment D1 wherein $R^2$ is $CH_3$.

Embodiment E1. The method described in the Summary of the Invention for preparing a compound of Formula 5 using the compound of Formula 1 prepared from the compounds of Formulae 2 and 3.

Embodiment E2. The method of Embodiment E1 wherein X is Cl.

Embodiment E3. The method of Embodiment E1 wherein X is Br.

Embodiment E4. The method of Embodiment E1 wherein Z is N.

Embodiment E5. The method of Embodiment E1 wherein $R^1$ is $C_1$-$C_4$ alkyl, cyclopropyl, cyclopropylmethyl or methylcyclopropyl.

Embodiment E6. The method of Embodiment E5 wherein $R^1$ is $C_1$-$C_4$ alkyl or cyclopropylmethyl.

Embodiment E7. The method of Embodiment E6 wherein $R^1$ is methyl.

Embodiment E8. The method of Embodiment E1 wherein $R^2$ is $CH_3$.

Embodiment E9. The method of Embodiment E1 wherein $R^4$ is Br.

Embodiment E10. The method of Embodiment E1 wherein $R^5$ is Cl.

Embodiment E11. The method of Embodiment E1 wherein $R^6$ is H.

Embodiment E12. The method of Embodiment E1 wherein $R^1$ is $CH_3$, $R^2$ is $CH_3$, $R^4$ is Br, $R^5$ is Cl, $R^6$ is H, X is Cl, and Z is N.

Embodiments of this invention can be combined in any manner.

The present methods and intermediate are described in further detail below. In the following Schemes the definitions of $R^1$, $R^2$, $R^3$, $R^4$, $R^5$, $R^6$, $R^7$, X and Z are as defined above unless otherwise stated.

As shown in Scheme 1, in a method of the present invention a substituted anthranilamide of Formula 1 is prepared by contacting from a substituted isatoic anhydride of Formula 2 with an amine of Formula 3 in the presence of a carboxylic acid.

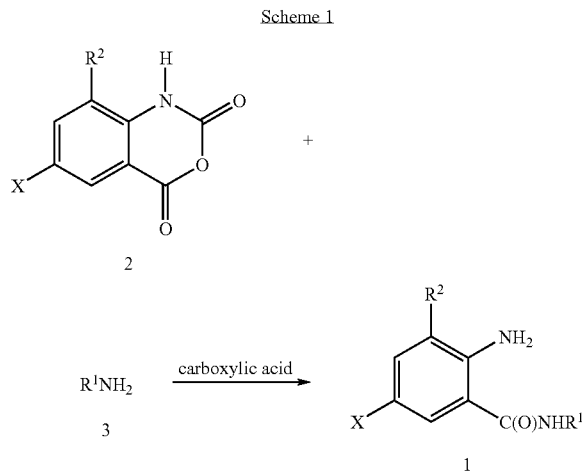

Scheme 1

As amines such as the compound of Formula 3 are bases, in the absence of the carboxylic acid the mixture of the compounds of Formulae 2 and 3 would be basic (e.g., effective pH>7). In the present method the carboxylic acid acts as a buffer to reduce the effective pH of the reaction mixture. A wide variety of carboxylic acids are useful in the present method, as the only requirement is for at least one carboxylic acid group to impart acidity. Other functional groups can be present, and more than one carboxylic acid group can be present on the carboxylic acid molecule. Typically the carboxylic acid in the present method has an effective $pK_a$ in the range of about 2 to about 5. Carboxylic acids include, for example, formic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid") is particularly preferred.

The combination of the carboxylic acid with the basic amine of Formula 3 forms an amine salt of the carboxylic acid. This amine salt can be preformed before addition of the isatoic anhydride compound of Formula 2, or the amine salt can be generated in situ by metering the amine of Formula 3 into a mixture of the compound of Formula 2 and the carboxylic acid. For either mode of addition, the present method is best carried out by maintaining the effective pH of the mixture during the reaction between about 3 and about 7.

As the effective pH of the mixture results from the buffering effect of the carboxylic acid in combination with the amine of Formula 3, the effective pH can be adjusted according to the effective $pK_a$ of the carboxylic acid by adjusting the molar ratio of carboxylic acid to amine of Formula 3. Typically the molar amounts of the amine of Formula 3 to carboxylic acid are in the range from about 0.6 to about 3, more typically from about 0.8 to about 3. More particularly, when the mode of combination involves metering the amine of Formula 3 into a mixture of the isatoic anhydride compound of Formula 2 and carboxylic acid, the molar ratio of Formula 3 amine to carboxylic acid is preferably from about 0.85 to about 3. When the mode of combination involves forming the amine salt before addition of the compound of Formula 2 the molar ratio of Formula 3 amine to carboxylic acid is preferably from about 0.8 to about 1.05; as long as a nearly equimolar ratio (e.g., about 0.95 to about 1.05) of Formula 3 amine to carboxylic acid is used, the amine salt thus formed is typically used in a ratio of about 1.1 to about 5 molar equivalents relative to the compound of Formula 2. For optimal conversions, the molar ratio of amine of Formula 3 to isatoic anhydride compound of Formula 2 should be at least 1.0, although the molar ratio is preferred to be from about 1.1 to about 1.5 for reasons of efficiency and economy, regardless of how the components are mixed. The molar amount of amine of Formula 3 relative to compound of Formula 2 can be substantially greater than 1.5, particularly when a nearly equimolar ratio (e.g., about 0.95 to about 1.05) of amine to acid is used.

The method of Scheme 1 typically achieves the highest product yield and purity when the reaction medium is substantially anhydrous. The reaction medium is thus typically formed from substantially anhydrous compounds of Formula 2 and 3 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 1 is typically conducted in a liquid phase. In many cases the reaction can be carried out without solvent other than the compounds of Formulae 1, 2 and 3 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 2 is typically from about 1 to about 20, and preferably about 5 for reasons of efficiency and economy.

The method of Scheme 1 forms carbon dioxide as a byproduct. As the method is typically conducted, most of the carbon dioxide formed evolves from the reaction medium as a gas. The addition of the compound of Formula 2 into reaction medium containing the amine of Formula 3 or the addition of the amine of Formula 3 into the reaction medium containing the compound of Formula 2 is preferably conducted at such a rate and temperature as to facilitate controlling the evolution of carbon dioxide. The temperature of the reaction medium is typically between about 5 and 75° C., more typically between about 35 and 60° C.

The product of Formula 1 can be isolated by standard techniques known in the art, including pH adjustment, extraction, evaporation, crystallization and chromatography. For example, the reaction medium can be diluted with about 3 to 15 parts by weight of water relative to the starting compound of Formula 2, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 1 are typically crystalline solids at ambient temperature, they are generally most easily isolated by filtration, optionally followed by washing with water and then drying. Typically no pH adjustment is needed during workup, and water is a useful crystallization medium for the products of Formula 1. Therefore a particularly convenient procedure is to dilute the reaction medium with water, remove most of the organic solvent by distillation at atmospheric pressure, and then cool the aqueous mixture to crystallize the product, which then can be collected by filtration. The method of Scheme 1 is illustrated by Examples 2-5 below.

As shown in Scheme 2, in another aspect of the present invention a substituted isatoic anhydride of Formula 2 is prepared by contacting a compound of Formula 4 with phosphorus tribromide.

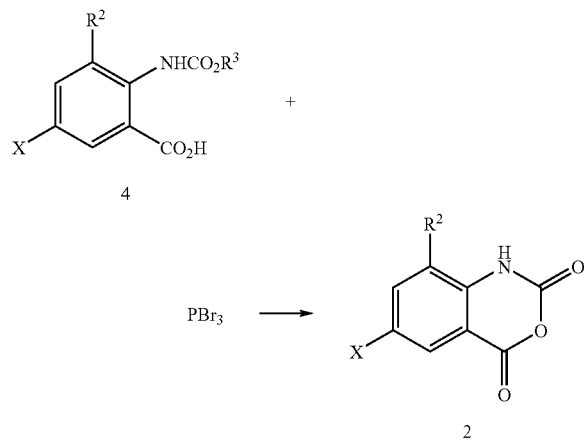

Scheme 2

Without being bound by any particular theory, phosphorus tribromide is believed to react with a compound of Formula 4 to produce a compound of Formula 10 as shown in Exhibit 1 as an intermediate along with hydrogen bromide, which subsequently react to form the compound of Formula 2 and $R^3Br$ as the ultimate byproduct.

Exhibit 1

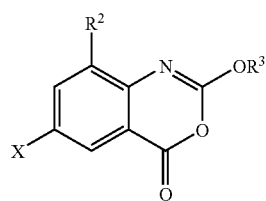

10

In the method of Scheme 2 the stoichiometric amount of phosphorus tribromide needed to obtain complete conversion of the compound of Formula 4 to the compound of Formula 2 is one-third molar equivalent. Typically the amount of phosphorus tribromide used is between about 0.3 and 3 molar equivalents, with about 0.33 to about 0.4 equivalents being preferred for reason of economy.

The method of Scheme 2 is typically conducted in a liquid phase, usually comprising a solvent to at least partially dissolve the compound of Formula 4. The solvent must be inert to phosphorus tribromide and preferably has a normal boiling point higher than 50° C., preferably greater than 70° C., to accommodate the reaction temperature. Examples of solvents suitable for this reaction are hydrocarbons (e.g., cyclohexane, benzene, toluene), halogenated hydrocarbons (e.g., 1-chlorobutane, 1,2-dichloroethane, chlorobenzene, o-dichlorobenzene), esters (e.g., n-butyl acetate) or nitriles (e.g., acetonitrile, benzonitrile).

The method of Scheme 2 can be conveniently carried out by diluting a compound of Formula 4 with a solvent and then adding phosphorus tribromide. Typically the phosphorus tribromide is added to the reaction mixture comprising the Formula 4 compound at such a rate that the temperature of the reaction mixture is maintained in the range between about 50 and 80° C. Preferably the rate of addition of phosphorus tribromide is selected to maintain the temperature of the reaction mixture in the range between about 60 and 75° C., as this controls the exothermic reaction and maximizes the purity of the product.

After completion of the reaction the product of Formula 2 can be isolated by standard techniques known in the art, including sparging, pH adjustment, extraction, evaporation, crystallization and chromatography. Much of the $R^3Br$ byproduct and hydrogen bromide remaining in the reaction mixture can be removed by sparging with air or a gas such as nitrogen. Compounds of Formula 2 are generally crystalline solids; on cooling the reaction mixture, the product usually crystallizes as a solid that can be collected by filtration, washed with water to remove residual phosphorous acid and hydrogen bromide, and dried. The method of Scheme 2 is illustrated by Example 1.

Compounds of Formula 4 can be prepared by general methods known in the art, including, for example halogenation of corresponding compounds of Formula 11 with chlorine or bromine as shown in Scheme 3.

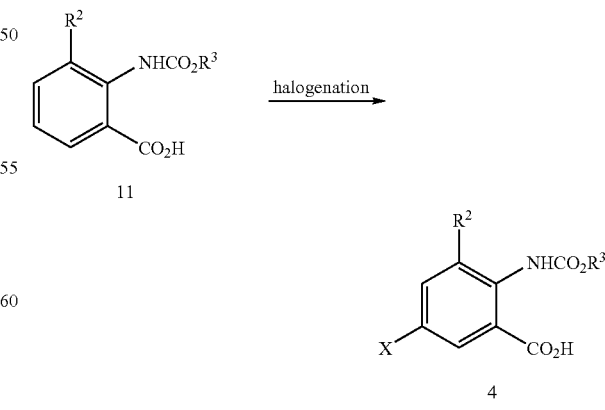

Scheme 3

Particularly useful for the halogenation of Scheme 3 is nascent chlorine or bromine generated by contact of aqueous hydrochloric acid or hydrobromic acid with hydrogen peroxide according to the general method of German Patent Publication DE 2750292-A1. This method is illustrated by Reference Example 1 for X being chlorine. Corresponding compounds can be prepared by this procedure by substituting hydrobromic acid for hydrochloric acid.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. Purity of products containing 2-amino-5-chloro-N,3-dimethylbenzamide was determined by Reverse Phase HPLC using an Ace C4 Column (Advanced Chromatography Technologies, Aberdeen, Scotland) and an acetonitrile/water gradient containing 0.005 M $NaH_2PO_4/H_2O$ buffer adjusted to pH 3 with $H_3PO_4$. $^1H$ NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet, and "br m" means broad multiplet.

REFERENCE EXAMPLE 1

Preparation of
5-Chloro-2-[(ethoxycarbonyl)amino]-3-methylbenzoic acid (a compound of Formula 4)

A 2-L reactor equipped with overhead stirrer and thermocouple was charged with 150 g (0.672 mol) of 2-[(ethoxycarbonyl)amino]-3-methylbenzoic acid (ca. 98% purity) and acetic acid (500 g). The resulting slurry was heated to 35-40° C. to give a solution, which was cooled to 30° C., and then hydrochloric acid (37%, 150 g, 1.5 mol, 2.2 eq) was added. The mixture was maintained at 30° C. while aqueous hydrogen peroxide (30%, 96 g, 0.85 mol, 1.25 eq) was added over about 1 h. The mixture was then warmed to 35° C. and held at that temperature for about 1 h. About 600 mL of water was metered in over about 30 minutes, while maintaining the temperature at 30-35° C. The mixture was cooled to 10° C., and the product was collected by filtration, and the wet cake was washed with water (3×100 mL); the third wash tested negative with KI-starch paper. The wet cake was dried to constant weight in a vacuum oven at 50° C. The crude yield was about 150 g (about 84% based on an estimated purity of 2-[(ethoxycarbonyl)amino]-3-methylbenzoic acid of 98% and estimated product purity of 95%). A portion of the crude product was first recrystallized from toluene and then recrystallized from aqueous methanol to give an analytical sample melting at 124-126° C.

$^1H$ NMR (DMSO-$d_6$) δ 1.19 (t, 3H), 2.22 (s, 3H), 4.05 (q, 2H), 7.54 (m, 2H), 8.9 (br s, 1H), 13.1 (brs, 1H).

EXAMPLE 1

Preparation of 6-Chloro-8-methyl-2H-3,1-benzoxazine-2,4(1H)-dione (a compound of Formula 2)

A 1-L, three-necked flask equipped with an addition funnel, thermometer, condenser, nitrogen bubbler, and caustic scrubber was charged with 5-chloro-2-[(ethoxy-carbonyl)amino]-3-methylbenzoic acid (i.e. the product of Reference Example 1) (74.0 g, 0.288 mol) and toluene (300 mL). The mixture was heated at 60-65° C. while phosphorus tribromide (39 g, 0.144 mol) was added over about 60 minutes. The mixture was heated at 65° C. for about 30 minutes, which resulted in no more than 0.2% of the intermediate 6-chloro-2-ethoxy-8-methyl-4H-3,1-benzoxazin-4-one remaining according to HPLC analysis. The mixture was sparged with nitrogen to remove hydrogen bromide and ethyl bromide, and then cooled to 20° C. The product was collected under filtration, and the filter cake was successively washed with toluene (30 mL) and water (2×100 mL), and then suction dried. Drying the collected solid in a vacuum oven to constant weight provided the title compound (59 g, about 97% purity by HPLC analysis). A portion of the dried product was recrystallized by dissolving in N,N-dimethylformamide (4 volumes) at 60° C. and cooling to 20° C. to provide a sample of 99% purity melting at >250° C.

$^1H$ NMR (DMSO-$d_6$) δ 2.33 (s, 3H), 7.67 (dd, 1H, J=2.5 and 0.6 Hz), 7.72 (d, 1H, J=2.4 Hz), 11.2 (br s, 1H).

EXAMPLE 2

Preparation of
2-Amino-5-chloro-N,3-dimethylbenzamide (a compound of Formula 1)

A 300-mL flask equipped with a thermometer and nitrogen bubbler was charged with ethyl acetate (100 mL) and 12.6 g (0.21 mol) of acetic acid. Anhydrous methylamine (6.3 g, 0.20 mol) was added below the surface of the liquid mixture, which was cooled to maintain the temperature below 35° C. Then 6-chloro-8-methyl-2H-3,1-benzoxazine-2,4(1H)-dione (21 g, 0.10 mol) (i.e. the product of Example 1) was added in portions while maintaining the reaction mixture at 35-40° C. After completion of the addition of the 6-chloro-8-methyl-2H-3,1-benzoxazine-2,4(1H)-dione the temperature was maintained at 40-45° C., and the progress of the reaction was monitored by HPLC analysis. After about 20 minutes, when no more than 0.5% 6-chloro-8-methyl-2H-3,1-benzoxazine-2,4(1H)-dione remained, water (50 mL) was added. A distillation head was attached, moderate vacuum was applied, and ethyl acetate was distilled out at an internal temperature of about 46-60° C. and pressure of about 30 to 50 kPa. To replace the ethyl acetate removed by distillation, water was added to maintain the original liquid volume in the reactor. When a significant amount of water began to distill, the aqueous slurry was cooled to 10° C. The solid was collected by filtration and dried at 60° C. and 13.3 kPa to afford the title compound as a white crystalline solid (19 g, ca. 95% yield, >98% purity by peak area in HPLC analysis).

EXAMPLE 3

A Second Preparation of
2-Amino-5-chloro-N,3-dimethylbenzamide

A 250-mL flask equipped with a thermometer and nitrogen bubbler was charged with 6-chloro-8-methyl-2H-3,1-benzoxazine-2,4(1H)-dione (9.0 g, 43 mmol) (i.e. the product of Example 1), ethyl acetate (50 mL), and acetic acid (3.8 g, 63 mmol). The mixture was heated to 50° C., and anhydrous methylamine (1.6 g, 50 mmol) was added below the surface of the mixture while maintaining the temperature at 48-52° C. The mixture was held for 1 h at 50° C., then water (65 mL) was added, and the ethyl acetate was removed by distillation.

When the pot temperature reached 83° C., the solution was seeded, and the product slurry was cooled over 3 h to 10° C. The solid was collected by filtration and dried to afford the title compound as a white crystalline solid (7.94 g, >98.5 wt. % purity by HPLC assay, 93% yield) melting at 143-145° C.

$^1$H NMR (DMSO-$d_6$) δ 2.08 (s, 3H), 2.72 (d, 3H, J=4.5 Hz), 6.36 (s, 2H), 7.13 (d, 1H, J=2.1 Hz), 7.40 (d, 1H, J=2.1 Hz), 8.33 (q, 1H, J=4.5 hz).

EXAMPLE 4

A Third Preparation of 2-Amino-5-chloro-N,3-dimethylbenzamide

A 250-mL flask equipped with thermometer and nitrogen bubbler was charged with 6-chloro-8-methyl-2H-3,1-benzoxazine-2,4(1H)-dione (21.0 g, 0.099 mol) (i.e. the product of Example 1), ethyl acetate (100 mL), and acetic acid (12.6 g, 0.21 mol). The mixture was stirred at 22° C., and anhydrous methylamine (4.3 g, 0.14 mol) was added below the surface of the mixture in portions over 45 minutes while maintaining the temperature at 22-41° C. The mixture was held for 2 h at 40° C., then water (150 mL) was added, and the ethyl acetate was removed by distillation. When the pot temperature reached 83° C., the solution was seeded, and the product slurry was cooled over about 2 h to 10° C. The solid was collected by filtration, washed with water and dried to afford the title compound as a white crystalline solid (18.38 g, >97.4 wt. % purity by HPLC, 94% yield) melting at 143-145° C.

EXAMPLE 5

Preparation of 2-Amino-5-chloro-N,3-dimethylbenzamide Using Aqueous Methylamine The procedure of Example 3 was modified by using aqueous methylamine (40% solution, 10.75 g, 0.138 mol) instead of anhydrous methylamine. Obtained after collection of solid and drying was 18.57 g of crude product, which HPLC showed containing the title compound in only 92.4 wt. % purity, thus corresponding to 87.3% yield. HPLC showed the crude product also containing about 3.4 wt. % of 6-chloro-3,8-dimethyl-2,4(1H,3H)-quinazolinedione derived from cyclization of the 5-chloro-3-methyl-2-[[(methylamino)-carbonyl]amino]benzoic acid by-product, and about 1.7% of the hydrolysis product 2-amino-5-chloro-3-methylbenzoic acid. This Example demonstrates that water has a detrimental effect on the yield and purity of the product.

Table 1 illustrates particular transformations to prepare compounds of Formula 1 according to a method of the present invention. For these transformations, the carboxylic acid is most conveniently acetic acid. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly; for example, "c-PrCH$_2$" means cyclopropylmethyl.

TABLE 1

| X | R$^1$ | R$^2$ |
|---|---|---|
| Cl | H | Me |
| Br | H | Me |
| Cl | Me | Me |
| Br | Me | Me |
| Cl | Et | Me |
| Br | Et | Me |
| Cl | i-Pr | Me |
| Br | i-Pr | Me |
| Cl | t-Bu | Me |
| Br | t-Bu | Me |
| Cl | c-Pr | Me |
| Br | c-Pr | Me |
| Cl | c-PrCH$_2$ | Me |
| Br | c-PrCH$_2$ | Me |
| Cl | 1-CH$_3$-c-Pr | Me |
| Br | 1-CH$_3$-c-Pr | Me |
| Cl | 2-CH$_3$-c-Pr | Me |
| Br | 2-CH$_3$-c-Pr | Me |
| Cl | H | Cl |
| Br | H | Cl |
| Cl | Me | Cl |
| Br | Me | Cl |
| Cl | Et | Cl |
| Br | Et | Cl |
| Cl | i-Pr | Cl |
| Br | i-Pr | Cl |
| Cl | t-Bu | Cl |
| Br | t-Bu | Cl |
| Cl | c-Pr | Cl |
| Br | c-Pr | Cl |
| Cl | c-PrCH$_2$ | Cl |
| Br | c-PrCH$_2$ | Cl |
| Cl | 1-CH$_3$-c-Pr | Cl |
| Br | 1-CH$_3$-c-Pr | Cl |
| Cl | 2-CH$_3$-c-Pr | Cl |
| Br | 2-CH3-c-Pr | Cl |

Table 2 illustrates particular transformations to prepare compounds of Formula 2 according to a method of the present invention.

TABLE 2

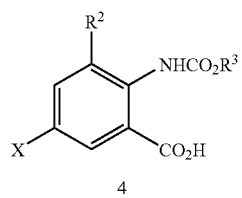

| X | R² | R³ |
|---|----|----|
| Cl | Me | Et |
| Br | Me | Et |
| Cl | Me | i-Pr |
| Br | Me | i-Pr |
| Cl | Me | Me |
| Br | Me | Me |
| Cl | Cl | n-Pr |
| Br | Me | allyl |
| Cl | Cl | benzyl |
| Br | Cl | benzyl |
| Cl | Cl | n-Bu |
| Br | Me | i-Bu |
| Cl | Cl | i-Bu |
| Br | Me | n-Bu |
| Cl | Me | benzyl |
| Br | Me | benzyl |
| Cl | Cl | Me |
| Br | Cl | Me |
| Cl | Cl | Et |
| Br | Cl | Et |
| Cl | Me | n-hexyl |
| Br | Me | n-hexyl |
| Cl | Me | 2-Cl-Et |
| Br | Me | 2-Cl-Et |

By the methods and procedures described herein together with methods known in the art, the compounds of Formula 4 listed in Table 3 can be prepared. In particular, these compounds are useful intermediates that can be made by the method of Scheme 3 and are starting materials for preparing compounds of Formula 2 according to the method of Scheme 2.

TABLE 3

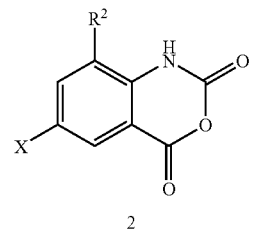

| X | R² | R³ |
|---|----|----|
| Cl | Me | Et |
| Br | Me | Et |

TABLE 3-continued

| X | R² | R³ |
|---|----|----|
| Cl | Me | i-Pr |
| Br | Me | i-Pr |
| Cl | Me | Me |
| Br | Me | Me |
| Cl | Cl | n-Pr |
| Br | Me | allyl |
| Cl | Cl | benzyl |
| Br | Cl | benzyl |
| Cl | Cl | n-Bu |
| Br | Me | i-Bu |
| Cl | Cl | i-Bu |
| Br | Me | n-Bu |
| Cl | Me | benzyl |
| Br | Me | benzyl |
| Cl | Cl | Me |
| Br | Cl | Me |
| Cl | Cl | Et |
| Br | Cl | Et |
| Cl | Me | n-hexyl |
| Br | Me | n-hexyl |
| Cl | Me | 2-Cl-Et |
| Br | Me | 2-Cl-Et |

Compounds of Formula 1 prepared by the present method of Scheme 1 are useful intermediates for preparing compounds of Formula 5.

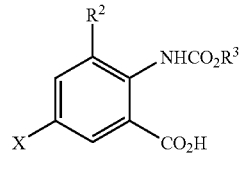

wherein
X is Cl or Br;
Z is $CR^7$ or N;
$R^1$ is H, $C_1$-$C_4$ alkyl, cyclopropyl, cyclopropylmethyl or methylcyclopropyl;
$R^2$ is $CH_3$ or Cl;
$R^4$ is Cl, Br, $CF_3$, $OCF_2H$ or $OCH_2CF_3$;
$R^5$ is F, Cl or Br;
$R^6$ is H, F or Cl; and
$R^7$ is H, F, Cl or Br.

Compounds of Formula 5 are useful as insecticides, as described, for example in PCT Patent Publications WO 2003/015518 and WO 2006/055922. A variety of routes are possible for preparing a compound of Formula 5 from a compound of Formula 1. In one method shown in Scheme 4, a compound of Formula 5 is prepared by combining a compound of Formula 1, a carboxylic acid compound of Formula 6 and sulfonyl chloride according to the general method taught in PCT Patent Publication WO 2006/062978, which is hereby incorporated herein in its entirety by reference.

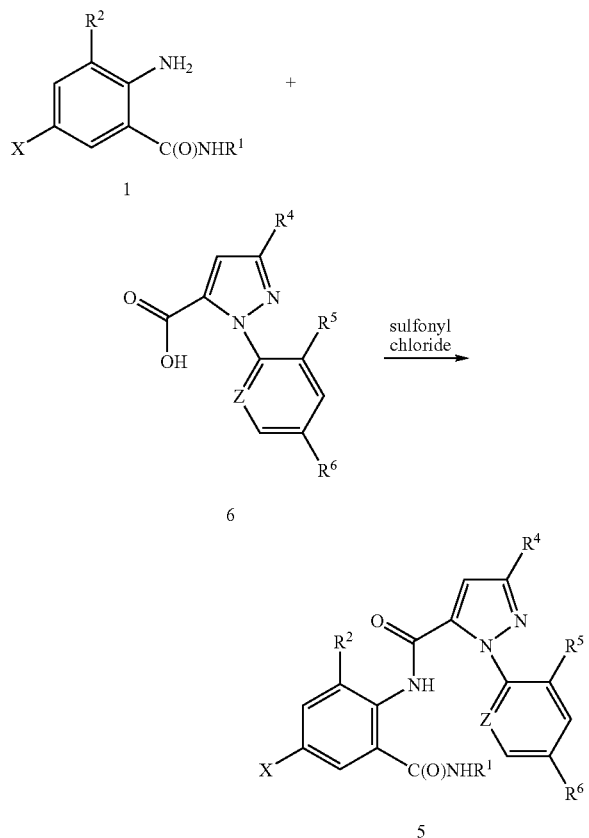

Scheme 4

As described in WO 2006/062978 a variety of reaction conditions are possible for this method. Typically a sulfonyl chloride is added to a mixture of the compounds of Formulae 1 and 6 in the presence of a solvent and a base. Sulfonyl chlorides are generally of the formula $RS(O)_2Cl$ wherein R is a carbon-based radical. Typically for this method R is $C_1$-$C_4$ alkyl, $C_1$-$C_2$ haloalkyl, or phenyl optionally substituted with 1-3 substituents selected from the group consisting of halogen, $C_1$-$C_3$ alkyl and nitro. Commercially available sulfonyl chlorides include methanesulfonyl chloride (R is $CH_3$), propanesulfonyl chloride (R is $(CH_2)_2CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 6 is stoichiometrically needed for complete conversion. Typically the molar ratio of sulfonyl chloride to the compound of Formula 6 is no more than about 2.5, more typically no more than about 1.4.

The compound of Formula 5 is formed when the starting compounds of Formulae 1 and 6 and the sulfonyl chloride are contacted with each other in a combined liquid phase, in which each is at least partially soluble. Particularly as the starting materials of Formulae 1 and 6 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 6 may have only slight solubility but its salt with added base may have more solubility in the solvent. Suitable solvents for this method include nitriles such as acetonitrile and propionitrile; esters such as methyl acetate, ethyl acetate, and butyl acetate; ketones such as acetone, methyl ethyl ketone (MEK), and methyl butyl ketone; haloalkanes such as dichloromethane and trichloromethane; ethers such as ethyl ether, methyl tert-butyl ether, tetrahydrofuran (THF), and p-dioxane; aromatic hydrocarbons such as benzene, toluene, chlorobenzene, and dichlorobenzene; tertiary amines such as trialkylamines, dialkylanilines, and optionally substituted pyridines; and mixtures of the foregoing. Solvents of note include acetonitrile, propionitrile, ethyl acetate, acetone, MEK, dichloromethane, methyl tert-butyl ether, THF, p-dioxane, toluene, and chlorobenzene. Of particular note as solvent is acetonitrile, as it often provides products in superior yield and/or purity.

As the reaction of the present method generates hydrogen chloride as a byproduct, which would otherwise bind to basic centers on the compounds of Formulae 1, 5 and 6, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 6 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as solvent the nominal mole ratio of the base charged to the sulfonyl chloride charged is typically from about 2.0 to 2.2, and is preferably from about 2.1 to 2.2. Preferred bases are tertiary amines, including substituted pyridines. More preferred bases include 2-picoline, 3-picoline, 2,6-lutidine, and pyridine. Of particular note as base is 3-picoline, as its salts with carboxylic acids of Formula 6 are often highly soluble in solvents such as acetonitrile.

The product N-phenylpyrazole-1-carboxamide compounds of Formula 5 can be isolated from the reaction mixtures by methods known to those skilled in the art, including crystallization, filtration, and extraction. WO 2006/062978 discloses specific examples relevant to the method of Scheme 4.

Pyrazolecarboxylic acid compounds of Formula 6 can be prepared using methods of heterocyclic synthesis known in the literature, including PCT Patent Publications WO 1998/57397, WO 2003/015519, WO 2006/055922 and WO 2006/062978 and references found in the following compendia: *Rodd's Chemistry of Chemistry of Carbon Compounds*, Vol. IVa to IVl, S. Coffey editor, Elsevier Scientific Publishing, New York, 1973; *Comprehensive Heterocyclic Chemistry*, Vol. 1-7, A. R. Katritzky and C. W. Rees editors, Pergamon Press, New York, 1984; *Comprehensive Heterocyclic Chemistry II*, Vol. 1-9, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York.

The method of Scheme 4 is illustrative of just one of many methods for converting an amine compound of Formula 1 to the corresponding carboxamide compound of Formula 5. A wide variety of general methods known in the art for preparing carboxamides from carboxylic acids and amines. For a general review, see M. North, *Contemporary Org. Synth.* 1995, 2, 269-287. Particular methods include contacting a compound of Formula 1 with a compound of Formula 6 in the presence of a dehydrating coupling agent such as 1,3-dicyclohexylcarbodiimide, 1,1'-carbonyldiimidazole, bis(2-oxo-3-oxazolidinyl)phosphinic chloride or benzotriazol-1-yloxy-tris(dimethylamino)phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed by the reference is the alternative of preparing an acyl chloride counterpart of the compound of Formula 6, such as by contact with thionyl chloride or oxalyl chloride in the presence of a catalytic amount of N,N-dimethylformamide, and then contacting the derived acyl chloride with the compound of Formula 1 in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product compounds of Formula 5 can be isolated from the reaction mixtures by methods known to those skilled in the art, including crystallization, filtration, and extraction.

Table 4 illustrates particular transformations to prepare compounds of Formula 5 from compounds of Formulae 2 and 3 according to a method of the present invention. The conversion of the compound of Formula 1 to the compound of Formula 5 can, for example, be accomplished according to the method of Scheme 4 using a sulfonyl chloride such as methanesulfonyl chloride in the presence of a solvent such as acetonitrile and a base such as 3-picoline.

TABLE 4

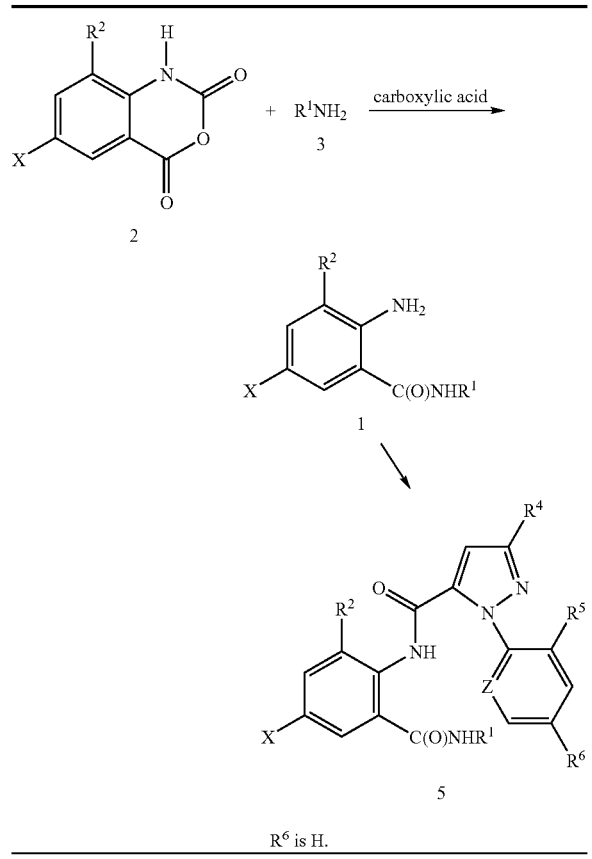

$R^6$ is H.

| X | $R^1$ | $R^2$ | $R^4$ | $R^5$ | Z |
|---|---|---|---|---|---|
| Cl | H | Me | $CF_3$ | F | N |
| Cl | Et | Me | $CF_3$ | F | N |
| Cl | t-Bu | Me | $CF_3$ | F | N |
| Cl | c-PrCH$_2$ | Me | $CF_3$ | F | N |
| Cl | Me | Me | $CF_3$ | Cl | N |
| Cl | i-Pr | Me | $CF_3$ | Cl | N |
| Cl | c-Pr | Me | $CF_3$ | Cl | N |
| Cl | 1-CH$_3$-c-Pr | Me | $CF_3$ | Cl | N |
| Cl | 2-CH$_3$-c-Pr | Me | $CF_3$ | Cl | N |
| Cl | H | Me | $CF_3$ | Br | N |
| Cl | Et | Me | $CF_3$ | Br | N |
| Cl | t-Bu | Me | $CF_3$ | Br | N |
| Cl | c-PrCH$_2$ | Me | $CF_3$ | Br | N |
| Cl | H | Me | Cl | F | N |
| Cl | Me | Me | Cl | F | N |
| Cl | Et | Me | Cl | F | N |
| Cl | i-Pr | Me | Cl | F | N |
| Cl | t-Bu | Me | Cl | F | N |
| Cl | c-Pr | Me | Cl | F | N |
| Cl | c-PrCH$_2$ | Me | Cl | F | N |
| Cl | 1-CH$_3$-c-Pr | Me | Cl | F | N |
| Cl | H | Me | Cl | Cl | N |
| Cl | Me | Me | Cl | Cl | N |
| Cl | Et | Me | Cl | Cl | N |
| Cl | i-Pr | Me | Cl | Cl | N |
| Cl | t-Bu | Me | Cl | Cl | N |
| Cl | c-Pr | Me | Cl | Cl | N |
| Cl | c-PrCH$_2$ | Me | Cl | Cl | N |
| Cl | 1-CH$_3$-c-Pr | Me | Cl | Cl | N |
| Cl | 2-CH$_3$-c-Pr | Me | Cl | Cl | N |
| Cl | H | Me | Cl | Br | N |
| Cl | Me | Me | Cl | Br | N |
| Cl | Et | Me | Cl | Br | N |
| Cl | i-Pr | Me | Cl | Br | N |
| Cl | t-Bu | Me | Cl | Br | N |
| Cl | c-Pr | Me | Cl | Br | N |
| Cl | c-PrCH$_2$ | Me | Cl | Br | N |
| Cl | 1-CH$_3$-c-Pr | Me | Cl | Br | N |
| Cl | H | Me | Br | F | N |
| Cl | Me | Me | Br | F | N |
| Cl | Et | Me | Br | F | N |
| Cl | i-Pr | Me | Br | F | N |
| Cl | t-Bu | Me | Br | F | N |
| Cl | c-Pr | Me | Br | F | N |
| Cl | c-PrCH$_2$ | Me | Br | F | N |
| Cl | 1-CH$_3$-c-Pr | Me | Br | F | N |
| Cl | H | Me | Br | Cl | N |
| Cl | Me | Me | Br | Cl | N |
| Cl | Et | Me | Br | Cl | N |
| Cl | i-Pr | Me | Br | Cl | N |
| Cl | t-Bu | Me | Br | Cl | N |
| Cl | c-Pr | Me | Br | Cl | N |
| Cl | c-PrCH$_2$ | Me | Br | Cl | N |
| Cl | 1-CH$_3$-c-Pr | Me | Br | Cl | N |
| Cl | 2-CH$_3$-c-Pr | Me | Br | Cl | N |
| Cl | H | Me | Br | Br | N |
| Cl | Me | Me | Br | Br | N |
| Cl | Et | Me | Br | Br | N |
| Cl | i-Pr | Me | Br | Br | N |
| Cl | t-Bu | Me | Br | Br | N |
| Cl | c-Pr | Me | Br | Br | N |
| Cl | c-PrCH$_2$ | Me | Br | Br | N |
| Cl | 1-CH$_3$-c-Pr | Me | Br | Br | N |
| Cl | H | Me | OCH$_2$CF$_3$ | F | N |
| Cl | Et | Me | OCH$_2$CF$_3$ | F | N |
| Cl | t-Bu | Me | OCH$_2$CF$_3$ | F | N |
| Cl | Me | Me | OCH$_2$CF$_3$ | Cl | N |
| Cl | i-Pr | Me | OCH$_2$CF$_3$ | Cl | N |
| Cl | Me | Me | OCH$_2$CF$_3$ | Br | N |
| Cl | i-Pr | Me | OCH$_2$CF$_3$ | Br | N |
| Cl | 1-CH$_3$-c-Pr | Me | OCH$_2$CF$_3$ | Br | N |
| Br | H | Me | $CF_3$ | F | N |
| Br | Et | Me | $CF_3$ | F | N |
| Br | t-Bu | Me | $CF_3$ | F | N |
| Br | c-PrCH$_2$ | Me | $CF_3$ | F | N |
| Br | Me | Me | $CF_3$ | Cl | N |
| Br | i-Pr | Me | $CF_3$ | Cl | N |
| Br | c-Pr | Me | $CF_3$ | Cl | N |
| Br | 1-CH$_3$-c-Pr | Me | $CF_3$ | Cl | N |
| Br | Et | Me | $CF_3$ | Br | N |
| Br | t-Bu | Me | $CF_3$ | Br | N |
| Br | c-PrCH$_2$ | Me | $CF_3$ | Br | N |
| Br | H | Me | Cl | F | N |
| Br | Me | Me | Cl | F | N |
| Br | Et | Me | Cl | F | N |
| Br | i-Pr | Me | Cl | F | N |
| Br | t-Bu | Me | Cl | F | N |
| Br | c-Pr | Me | Cl | F | N |
| Br | c-PrCH$_2$ | Me | Cl | F | N |

TABLE 4-continued

| | | | | | |
|---|---|---|---|---|---|
| Br | 1-CH₃-c-Pr | Me | Cl | F | N |
| Br | H | Me | Cl | Cl | N |
| Br | Me | Me | Cl | Cl | N |
| Br | Et | Me | Cl | Cl | N |
| Br | i-Pr | Me | Cl | Cl | N |
| Br | t-Bu | Me | Cl | Cl | N |
| Br | c-Pr | Me | Cl | Cl | N |
| Br | c-PrCH₂ | Me | Cl | Cl | N |
| Br | 1-CH₃-c-Pr | Me | Cl | Cl | N |
| Br | H | Me | Cl | Br | N |
| Br | Me | Me | Cl | Br | N |
| Br | Et | Me | Cl | Br | N |
| Br | i-Pr | Me | Cl | Br | N |
| Br | t-Bu | Me | Cl | Br | N |
| Br | c-Pr | Me | Cl | Br | N |
| Br | c-PrCH₂ | Me | Cl | Br | N |
| Br | 1-CH₃-c-Pr | Me | Cl | Br | N |
| Br | H | Me | Br | F | N |
| Br | Me | Me | Br | F | N |
| Br | Et | Me | Br | F | N |
| Br | i-Pr | Me | Br | F | N |
| Br | t-Bu | Me | Br | F | N |
| Br | c-Pr | Me | Br | F | N |
| Br | c-PrCH₂ | Me | Br | F | N |
| Br | 1-CH₃-c-Pr | Me | Br | F | N |
| Br | H | Me | Br | Cl | N |
| Br | Me | Me | Br | Cl | N |
| Br | Et | Me | Br | Cl | N |
| Br | i-Pr | Me | Br | Cl | N |
| Br | t-Bu | Me | Br | Cl | N |
| Br | c-Pr | Me | Br | Cl | N |
| Br | c-PrCH₂ | Me | Br | Cl | N |
| Br | 1-CH₃-c-Pr | Me | Br | Cl | N |
| Br | H | Me | Br | Br | N |
| Br | Me | Me | Br | Br | N |
| Br | Et | Me | Br | Br | N |
| Br | i-Pr | Me | Br | Br | N |
| Br | t-Bu | Me | Br | Br | N |
| Br | c-Pr | Me | Br | Br | N |
| Br | c-PrCH₂ | Me | Br | Br | N |
| Br | 1-CH₃-c-Pr | Me | Br | Br | N |
| Br | H | Me | OCH₂CF₃ | F | N |
| Br | Et | Me | OCH₂CF₃ | F | N |
| Br | t-Bu | Me | OCH₂CF₃ | F | N |
| Br | Me | Me | OCH₂CF₃ | Cl | N |
| Br | i-Pr | Me | OCH₂CF₃ | Cl | N |
| Br | Me | Me | OCH₂CF₃ | Br | N |
| Br | i-Pr | Me | OCH₂CF₃ | Br | N |
| Cl | H | Me | OCHF₂ | F | N |
| Cl | Et | Me | OCHF₂ | F | N |
| Cl | t-Bu | Me | OCHF₂ | F | N |
| Cl | Me | Me | OCHF₂ | Cl | N |
| Cl | i-Pr | Me | OCHF₂ | Cl | N |
| Cl | H | Me | OCHF₂ | Br | N |
| Cl | Et | Me | OCHF₂ | Br | N |
| Cl | t-Bu | Me | OCHF₂ | Br | N |
| Br | Me | Me | OCHF₂ | F | N |
| Br | i-Pr | Me | OCHF₂ | F | N |
| Br | H | Me | OCHF₂ | Cl | N |
| Br | Et | Me | OCHF₂ | Cl | N |
| Br | t-Bu | Me | OCHF₂ | Cl | N |
| Br | Me | Me | OCHF₂ | Br | N |
| Br | i-Pr | Me | OCHF₂ | Br | N |
| Cl | H | Me | CF₃ | F | CH |
| Cl | Et | Me | CF₃ | F | CH |
| Cl | t-Bu | Me | CF₃ | F | CH |
| Cl | c-PrCH₂ | Me | CF₃ | F | CH |
| Cl | Me | Me | CF₃ | Cl | CH |
| Cl | i-Pr | Me | CF₃ | Cl | CH |
| Cl | c-Pr | Me | CF₃ | Cl | CH |
| Cl | 1-CH₃-c-Pr | Me | CF₃ | Cl | CH |
| Cl | H | Me | CF₃ | Br | CH |
| Cl | Et | Me | CF₃ | Br | CH |
| Cl | t-Bu | Me | CF₃ | Br | CH |
| Cl | c-PrCH₂ | Me | CF₃ | Br | CH |
| Cl | H | Me | Cl | F | CH |
| Cl | Me | Me | Cl | F | CH |
| Cl | Et | Me | Cl | F | CH |
| Cl | i-Pr | Me | Cl | F | CH |
| Cl | t-Bu | Me | Cl | F | CH |
| Cl | c-Pr | Me | Cl | F | CH |
| Cl | c-PrCH₂ | Me | Cl | F | CH |
| Cl | 1-CH₃-c-Pr | Me | Cl | F | CH |
| Cl | H | Me | Cl | Cl | CH |
| Cl | Me | Me | Cl | Cl | CH |
| Cl | Et | Me | Cl | Cl | CH |
| Cl | i-Pr | Me | Cl | Cl | CH |
| Cl | t-Bu | Me | Cl | Cl | CH |
| Cl | c-Pr | Me | Cl | Cl | CH |
| Cl | c-PrCH₂ | Me | Cl | Cl | CH |
| Cl | 1-CH₃-c-Pr | Me | Cl | Cl | CH |
| Cl | H | Me | Cl | Br | CH |
| Cl | Me | Me | Cl | Br | CH |
| Cl | Et | Me | Cl | Br | CH |
| Cl | i-Pr | Me | Cl | Br | CH |
| Cl | t-Bu | Me | Cl | Br | CH |
| Cl | c-Pr | Me | Cl | Br | CH |
| Cl | c-PrCH₂ | Me | Cl | Br | CH |
| Cl | 1-CH₃-c-Pr | Me | Cl | Br | CH |
| Cl | H | Me | Br | F | CH |
| Cl | Me | Me | Br | F | CH |
| Cl | Et | Me | Br | F | CH |
| Cl | i-Pr | Me | Br | F | CH |
| Cl | t-Bu | Me | Br | F | CH |
| Cl | c-Pr | Me | Br | F | CH |
| Cl | c-PrCH₂ | Me | Br | F | CH |
| Cl | 1-CH₃-c-Pr | Me | Br | F | CH |
| Cl | H | Me | Br | Cl | CH |
| Cl | Me | Me | Br | Cl | CH |
| Cl | Et | Me | Br | Cl | CH |
| Cl | i-Pr | Me | Br | Cl | CH |
| Cl | t-Bu | Me | Br | Cl | CH |
| Cl | c-Pr | Me | Br | Cl | CH |
| Cl | c-PrCH₂ | Me | Br | Cl | CH |
| Cl | 1-CH₃-c-Pr | Me | Br | Cl | CH |
| Cl | H | Me | Br | Br | CH |
| Cl | Me | Me | Br | Br | CH |
| Cl | Et | Me | Br | Br | CH |
| Cl | i-Pr | Me | Br | Br | CH |
| Cl | t-Bu | Me | Br | Br | CH |
| Cl | c-Pr | Me | Br | Br | CH |
| Cl | c-PrCH₂ | Me | Br | Br | CH |
| Cl | 1-CH₃-c-Pr | Me | Br | Br | CH |
| Cl | H | Me | OCH₂CF₃ | F | CH |
| Cl | Et | Me | OCH₂CF₃ | F | CH |
| Cl | t-Bu | Me | OCH₂CF₃ | F | CH |
| Cl | Me | Me | OCH₂CF₃ | Cl | CH |
| Cl | i-Pr | Me | OCH₂CF₃ | Cl | CH |
| Cl | H | Me | OCH₂CF₃ | Br | CH |
| Cl | Et | Me | OCH₂CF₃ | Br | CH |
| Cl | t-Bu | Me | OCH₂CF₃ | Br | CH |
| Br | Me | Me | CF₃ | F | CH |
| Br | i-Pr | Me | CF₃ | F | CH |
| Br | c-Pr | Me | CF₃ | F | CH |
| Br | H | Me | CF₃ | Cl | CH |
| Br | Et | Me | CF₃ | Cl | CH |
| Br | t-Bu | Me | CF₃ | Cl | CH |
| Br | c-PrCH₂ | Me | CF₃ | Cl | CH |
| Br | 1-CH₃-c-Pr | Me | CF₃ | Cl | CH |
| Br | Me | Me | CF₃ | Br | CH |
| Br | i-Pr | Me | CF₃ | Br | CH |
| Br | c-Pr | Me | CF₃ | Br | CH |
| Br | H | Me | Cl | F | CH |
| Br | Me | Me | Cl | F | CH |
| Br | Et | Me | Cl | F | CH |
| Br | i-Pr | Me | Cl | F | CH |
| Br | t-Bu | Me | Cl | F | CH |
| Br | c-Pr | Me | Cl | F | CH |
| Br | c-PrCH₂ | Me | Cl | F | CH |
| Br | 1-CH₃-c-Pr | Me | Cl | F | CH |
| Br | H | Me | Cl | Cl | CH |
| Br | Me | Me | Cl | Cl | CH |
| Br | Et | Me | Cl | Cl | CH |
| Br | i-Pr | Me | Cl | Cl | CH |
| Br | t-Bu | Me | Cl | Cl | CH |
| Br | c-Pr | Me | Cl | Cl | CH |
| Br | c-PrCH₂ | Me | Cl | Cl | CH |
| Br | 1-CH₃-c-Pr | Me | Cl | Cl | CH |
| Br | H | Me | Cl | Br | CH |
| Br | Me | Me | Cl | Br | CH |
| Br | Et | Me | Cl | Br | CH |
| Br | i-Pr | Me | Cl | Br | CH |
| Br | t-Bu | Me | Cl | Br | CH |

TABLE 4-continued

| | | | | | |
|---|---|---|---|---|---|
| Br | c-Pr | Me | Cl | Br | CH |
| Br | c-PrCH$_2$ | Me | Cl | Br | CH |
| Br | 1-CH$_3$-c-Pr | Me | Cl | Br | CH |
| Br | H | Me | Br | F | CH |
| Br | Me | Me | Br | F | CH |
| Br | Et | Me | Br | F | CH |
| Br | i-Pr | Me | Br | F | CH |
| Br | t-Bu | Me | Br | F | CH |
| Br | c-Pr | Me | Br | F | CH |
| Br | c-PrCH$_2$ | Me | Br | F | CH |
| Br | 1-CH$_3$-c-Pr | Me | Br | F | CH |
| Br | H | Me | Br | Cl | CH |
| Br | Me | Me | Br | Cl | CH |
| Br | Et | Me | Br | Cl | CH |
| Br | i-Pr | Me | Br | Cl | CH |
| Br | t-Bu | Me | Br | Cl | CH |
| Br | c-Pr | Me | Br | Cl | CH |
| Br | c-PrCH$_2$ | Me | Br | Cl | CH |
| Br | 1-CH$_3$-c-Pr | Me | Br | Cl | CH |
| Br | H | Me | Br | Br | CH |
| Br | Me | Me | Br | Br | CH |
| Br | Et | Me | Br | Br | CH |
| Br | i-Pr | Me | Br | Br | CH |
| Br | t-Bu | Me | Br | Br | CH |
| Br | H | Me | OCH$_2$CF$_3$ | F | CH |
| Br | Et | Me | OCH$_2$CF$_3$ | F | CH |
| Br | t-Bu | Me | OCH$_2$CF$_3$ | F | CH |
| Br | Me | Me | OCH$_2$CF$_3$ | Cl | CH |
| Br | i-Pr | Me | OCH$_2$CF$_3$ | Cl | CH |
| Br | H | Me | OCH$_2$CF$_3$ | Br | CH |
| Br | Et | Me | OCH$_2$CF$_3$ | Br | CH |
| Br | t-Bu | Me | OCH$_2$CF$_3$ | Br | CH |
| Cl | Me | Me | OCHF$_2$ | F | CH |
| Cl | i-Pr | Me | OCHF$_2$ | F | CH |
| Cl | H | Me | OCHF$_2$ | Cl | CH |
| Cl | Et | Me | OCHF$_2$ | Cl | CH |
| Cl | t-Bu | Me | OCHF$_2$ | Cl | CH |
| Cl | Me | Me | OCHF$_2$ | Br | CH |
| Cl | i-Pr | Me | OCHF$_2$ | Br | CH |
| Br | H | Me | OCHF$_2$ | F | CH |
| Br | Et | Me | OCHF$_2$ | F | CH |
| Br | t-Bu | Me | OCHF$_2$ | F | CH |
| Br | Me | Me | OCHF$_2$ | Cl | CH |
| Br | i-Pr | Me | OCHF$_2$ | Cl | CH |
| Br | H | Me | OCHF$_2$ | Br | CH |
| Br | Et | Me | OCHF$_2$ | Br | CH |
| Br | t-Bu | Me | OCHF$_2$ | Br | CH |
| Cl | Me | Cl | CF$_3$ | F | N |
| Cl | i-Pr | Cl | CF$_3$ | F | N |
| Cl | c-Pr | Cl | CF$_3$ | F | N |
| Cl | 1-CH$_3$-c-Pr | Cl | CF$_3$ | F | N |
| Cl | H | Cl | CF$_3$ | Cl | N |
| Cl | Et | Cl | CF$_3$ | Cl | N |
| Cl | t-Bu | Cl | CF$_3$ | Cl | N |
| Cl | c-PrCH$_2$ | Cl | CF$_3$ | Cl | N |
| Cl | Me | Cl | CF$_3$ | Br | N |
| Cl | i-Pr | Cl | CF$_3$ | Br | N |
| Cl | c-Pr | CH$_3$ | CF$_3$ | Br | N |
| Cl | 1-CH$_3$-c-Pr | CH$_3$ | CF$_3$ | Br | N |
| Cl | H | Cl | Cl | F | N |
| Cl | Me | Cl | Cl | F | N |
| Cl | Et | Cl | Cl | F | N |
| Cl | i-Pr | Cl | Cl | F | N |
| Cl | t-Bu | Cl | Cl | F | N |
| Cl | c-Pr | Cl | Cl | F | N |
| Cl | c-PrCH$_2$ | Cl | Cl | F | N |
| Cl | 1-CH$_3$-c-Pr | Cl | Cl | F | N |
| Cl | H | Cl | Cl | Cl | N |
| Cl | Me | Cl | Cl | Cl | N |
| Cl | Et | Cl | Cl | Cl | N |
| Cl | i-Pr | Cl | Cl | Cl | N |
| Cl | t-Bu | Cl | Cl | Cl | N |
| Cl | c-Pr | Cl | Cl | Cl | N |
| Cl | c-PrCH$_2$ | Cl | Cl | Cl | N |
| Cl | 1-CH$_3$-c-Pr | Cl | Cl | Cl | N |
| Cl | H | Cl | Cl | Br | N |
| Cl | Me | Cl | Cl | Br | N |
| Cl | Et | Cl | Cl | Br | N |
| Cl | i-Pr | Cl | Cl | Br | N |
| Cl | t-Bu | Cl | Cl | Br | N |

TABLE 4-continued

| | | | | | |
|---|---|---|---|---|---|
| Cl | c-Pr | Cl | Cl | Br | N |
| Cl | c-PrCH$_2$ | Cl | Cl | Br | N |
| Cl | 1-CH$_3$-c-Pr | Cl | Cl | Br | N |
| Cl | H | Cl | Br | F | N |
| Cl | Me | Cl | Br | F | N |
| Cl | Et | Cl | Br | F | N |
| Cl | i-Pr | Cl | Br | F | N |
| Cl | t-Bu | Cl | Br | F | N |
| Cl | c-Pr | Cl | Br | F | N |
| Cl | c-PrCH$_2$ | Cl | Br | F | N |
| Cl | 1-CH$_3$-c-Pr | Cl | Br | F | N |
| Cl | H | Cl | Br | Cl | N |
| Cl | Me | Cl | Br | Cl | N |
| Cl | Et | Cl | Br | Cl | N |
| Cl | i-Pr | Cl | Br | Cl | N |
| Cl | t-Bu | Cl | Br | Cl | N |
| Cl | c-Pr | Cl | Br | Cl | N |
| Cl | c-PrCH$_2$ | Cl | Br | Cl | N |
| Cl | 1-CH$_3$-c-Pr | Cl | Br | Cl | N |
| Cl | H | Cl | Br | Br | N |
| Cl | Me | Cl | Br | Br | N |
| Cl | Et | Cl | Br | Br | N |
| Cl | i-Pr | Cl | Br | Br | N |
| Cl | t-Bu | Cl | Br | Br | N |
| Cl | c-Pr | Cl | Br | Br | N |
| Cl | c-PrCH$_2$ | Cl | Br | Br | N |
| Cl | 1-CH$_3$-c-Pr | Cl | Br | Br | N |
| Cl | Me | Cl | OCH2CF$_3$ | F | N |
| Cl | i-Pr | Cl | OCH2CF$_3$ | F | N |
| Cl | H | Cl | OCH$_2$CF$_3$ | Cl | N |
| Cl | Et | Cl | OCH$_2$CF$_3$ | Cl | N |
| Cl | t-Bu | Cl | OCH$_2$CF$_3$ | Cl | N |
| Cl | H | Cl | OCH$_2$CF$_3$ | Br | N |
| Cl | Et | Cl | OCH$_2$CF$_3$ | Br | N |
| Cl | t-Bu | Cl | OCH$_2$CF$_3$ | Br | N |
| Br | Me | Cl | CF$_3$ | F | N |
| Br | i-Pr | Cl | CF$_3$ | F | N |
| Br | c-Pr | Cl | CF$_3$ | F | N |
| Br | 1-CH$_3$-c-Pr | Cl | CF$_3$ | F | N |
| Br | H | Cl | CF$_3$ | Cl | N |
| Br | Et | Cl | CF$_3$ | Cl | N |
| Br | t-Bu | Cl | CF$_3$ | Cl | N |
| Br | c-PrCH$_2$ | Cl | CF$_3$ | Cl | N |
| Br | H | Cl | CF$_3$ | Br | N |
| Br | Me | Cl | CF$_3$ | Br | N |
| Br | i-Pr | Cl | CF$_3$ | Br | N |
| Br | c-Pr | Cl | CF$_3$ | Br | N |
| Br | 1-CH$_3$-c-Pr | Cl | CF$_3$ | Br | N |
| Br | H | Cl | Cl | F | N |
| Br | Me | Cl | Cl | F | N |
| Br | Et | Cl | Cl | F | N |
| Br | i-Pr | Cl | Cl | F | N |
| Br | t-Bu | Cl | Cl | F | N |
| Br | c-Pr | Cl | Cl | F | N |
| Br | c-PrCH$_2$ | Cl | Cl | F | N |
| Br | 1-CH$_3$-c-Pr | Cl | Cl | F | N |
| Br | H | Cl | Cl | Cl | N |
| Br | Me | Cl | Cl | Cl | N |
| Br | Et | Cl | Cl | Cl | N |
| Br | i-Pr | Cl | Cl | Cl | N |
| Br | t-Bu | Cl | Cl | Cl | N |
| Br | c-Pr | Cl | Cl | Cl | N |
| Br | c-PrCH$_2$ | Cl | Cl | Cl | N |
| Br | 1-CH$_3$-c-Pr | Cl | Cl | Cl | N |
| Br | H | Cl | Cl | Br | N |
| Br | Me | Cl | Cl | Br | N |
| Br | Et | Cl | Cl | Br | N |
| Br | i-Pr | Cl | Cl | Br | N |
| Br | t-Bu | Cl | Cl | Br | N |
| Br | c-Pr | Cl | Cl | Br | N |
| Br | c-PrCH$_2$ | Cl | Cl | Br | N |
| Br | 1-CH$_3$-c-Pr | Cl | Cl | Br | N |
| Br | H | Cl | Br | F | N |
| Br | Me | Cl | Br | F | N |
| Br | Et | Cl | Br | F | N |
| Br | i-Pr | Cl | Br | F | N |
| Br | t-Bu | Cl | Br | F | N |
| Br | c-Pr | Cl | Br | F | N |
| Br | c-PrCH$_2$ | Cl | Br | F | N |
| Br | 1-CH$_3$-c-Pr | Cl | Br | F | N |

TABLE 4-continued

| | | | | | | | | | | | |
|---|---|---|---|---|---|---|---|---|---|---|---|
| Br | H | Cl | Br | Cl | N | Cl | c-Pr | Cl | Br | F | CH |
| Br | Me | Cl | Br | Cl | N | Cl | c-PrCH$_2$ | Cl | Br | F | CH |
| Br | Et | Cl | Br | Cl | N | Cl | 1-CH$_3$-c-Pr | Cl | Br | F | CH |
| Br | i-Pr | Cl | Br | Cl | N | Cl | H | Cl | Br | Cl | CH |
| Br | t-Bu | Cl | Br | Cl | N | Cl | Me | Cl | Br | Cl | CH |
| Br | c-Pr | Cl | Br | Cl | N | Cl | Et | Cl | Br | Cl | CH |
| Br | c-PrCH$_2$ | Cl | Br | Cl | N | Cl | i-Pr | Cl | Br | Cl | CH |
| Br | 1-CH$_3$-c-Pr | Cl | Br | Cl | N | Cl | t-Bu | Cl | Br | Cl | CH |
| Br | H | Cl | Br | Br | N | Cl | c-Pr | Cl | Br | Cl | CH |
| Br | Me | Cl | Br | Br | N | Cl | c-PrCH$_2$ | Cl | Br | Cl | CH |
| Br | Et | Cl | Br | Br | N | Cl | 1-CH$_3$-c-Pr | Cl | Br | Cl | CH |
| Br | i-Pr | Cl | Br | Br | N | Cl | H | Cl | Br | Br | CH |
| Br | t-Bu | Cl | Br | Br | N | Cl | Me | Cl | Br | Br | CH |
| Br | c-Pr | Cl | Br | Br | N | Cl | Et | Cl | Br | Br | CH |
| Br | c-PrCH$_2$ | Cl | Br | Br | N | Cl | i-Pr | Cl | Br | Br | CH |
| Br | 1-CH$_3$-c-Pr | Cl | Br | Br | N | Cl | t-Bu | Cl | Br | Br | CH |
| Br | Me | Cl | OCH$_2$CF$_3$ | F | N | Cl | Me | Cl | OCH$_2$CF$_3$ | F | CH |
| Br | i-Pr | Cl | OCH$_2$CF$_3$ | F | N | Cl | i-Pr | Cl | OCH$_2$CF$_3$ | F | CH |
| Br | H | Cl | OCH$_2$CF$_3$ | Cl | N | Cl | H | Cl | OCH$_2$CF$_3$ | Cl | CH |
| Br | Et | Cl | OCH$_2$CF$_3$ | Cl | N | Cl | Et | Cl | OCH$_2$CF$_3$ | Cl | CH |
| Br | t-Bu | Cl | OCH$_2$CF$_3$ | Cl | N | Cl | t-Bu | Cl | OCH$_2$CF$_3$ | Cl | CH |
| Br | H | Cl | OCH$_2$CF$_3$ | Br | N | Cl | Me | Cl | OCH$_2$CF$_3$ | Br | CH |
| Br | Et | Cl | OCH$_2$CF$_3$ | Br | N | Cl | i-Pr | Cl | OCH$_2$CF$_3$ | Br | CH |
| Br | t-Bu | Cl | OCH$_2$CF$_3$ | Br | N | Br | H | Cl | CF$_3$ | F | CH |
| Cl | Me | Cl | OCHF$_2$ | F | N | Br | Et | Cl | CF$_3$ | F | CH |
| Cl | i-Pr | Cl | OCHF$_2$ | F | N | Br | t-Bu | Cl | CF$_3$ | F | CH |
| Cl | H | Cl | OCHF$_2$ | Cl | N | Br | c-PrCH$_2$ | Cl | CF$_3$ | F | CH |
| Cl | Et | Cl | OCHF$_2$ | Cl | N | Br | 1-CH$_3$-c-Pr | Cl | CF$_3$ | F | CH |
| Cl | t-Bu | Cl | OCHF$_2$ | Cl | N | Br | Me | Cl | CF$_3$ | Cl | CH |
| Cl | Me | Cl | OCHF$_2$ | Br | N | Br | i-Pr | Cl | CF$_3$ | Cl | CH |
| Cl | i-Pr | Cl | OCHF$_2$ | Br | N | Br | c-Pr | Cl | CF$_3$ | Cl | CH |
| Br | H | Cl | OCHF$_2$ | F | N | Br | H | Cl | CF$_3$ | Br | CH |
| Br | Et | Cl | OCHF$_2$ | F | N | Br | Et | Cl | CF$_3$ | Br | CH |
| Br | t-Bu | Cl | OCHF$_2$ | F | N | Br | t-Bu | Cl | CF$_3$ | Br | CH |
| Br | Me | Cl | OCHF$_2$ | Cl | N | Br | c-PrCH$_2$ | Cl | CF$_3$ | Br | CH |
| Br | i-Pr | Cl | OCHF$_2$ | Cl | N | Br | 1-CH$_3$-c-Pr | Cl | CF$_3$ | Br | CH |
| Br | H | Cl | OCHF$_2$ | Br | N | Br | H | Cl | Cl | F | CH |
| Br | Et | Cl | OCHF$_2$ | Br | N | Br | Me | Cl | Cl | F | CH |
| Br | t-Bu | Cl | OCHF$_2$ | Br | N | Br | Et | Cl | Cl | F | CH |
| Cl | Me | Cl | CF$_3$ | F | CH | Br | i-Pr | Cl | Cl | F | CH |
| Cl | i-Pr | Cl | CF$_3$ | F | CH | Br | t-Bu | Cl | Cl | F | CH |
| Cl | c-Pr | Cl | CF$_3$ | F | CH | Br | c-Pr | Cl | Cl | F | CH |
| Cl | 1-CH$_3$-c-Pr | Cl | CF$_3$ | F | CH | Br | c-PrCH$_2$ | Cl | Cl | F | CH |
| Cl | H | Cl | CF$_3$ | Cl | CH | Br | 1-CH$_3$-c-Pr | Cl | Cl | F | CH |
| Cl | Et | Cl | CF$_3$ | Cl | CH | Br | H | Cl | Cl | Cl | CH |
| Cl | t-Bu | Cl | CF$_3$ | Cl | CH | Br | Me | Cl | Cl | Cl | CH |
| Cl | c-PrCH$_2$ | Cl | CF$_3$ | Cl | CH | Br | Et | Cl | Cl | Cl | CH |
| Cl | Me | Cl | CF$_3$ | Br | CH | Br | i-Pr | Cl | Cl | Cl | CH |
| Cl | i-Pr | Cl | CF$_3$ | Br | CH | Br | t-Bu | Cl | Cl | Cl | CH |
| Cl | c-Pr | Cl | CF$_3$ | Br | CH | Br | c-Pr | Cl | Cl | Cl | CH |
| Cl | 1-CH$_3$-c-Pr | Cl | CF$_3$ | Br | CH | Br | c-PrCH$_2$ | Cl | Cl | Cl | CH |
| Cl | H | Cl | Cl | F | CH | Br | 1-CH$_3$-c-Pr | Cl | Cl | Cl | CH |
| Cl | Me | Cl | Cl | F | CH | Br | H | Cl | Cl | Br | CH |
| Cl | Et | Cl | Cl | F | CH | Br | Me | Cl | Cl | Br | CH |
| Cl | i-Pr | Cl | Cl | F | CH | Br | Et | Cl | Cl | Br | CH |
| Cl | t-Bu | Cl | Cl | F | CH | Br | i-Pr | Cl | Cl | Br | CH |
| Cl | c-Pr | Cl | Cl | F | CH | Br | t-Bu | Cl | Cl | Br | CH |
| Cl | c-PrCH$_2$Cl | Cl | Cl | F | CH | Br | c-Pr | Cl | Cl | Br | CH |
| Cl | 1-CH$_3$-c-Pr | Cl | Cl | F | CH | Br | c-PrCH$_2$ | Cl | Cl | Br | CH |
| Cl | H | Cl | Cl | Cl | CH | Br | 1-CH$_3$-c-Pr | Cl | Cl | Br | CH |
| Cl | Me | Cl | Cl | Cl | CH | Br | H | Cl | Br | F | CH |
| Cl | Et | Cl | Cl | Cl | CH | Br | Me | Cl | Br | F | CH |
| Cl | i-Pr | Cl | Cl | Cl | CH | Br | Et | Cl | Br | F | CH |
| Cl | t-Bu | Cl | Cl | Cl | CH | Br | i-Pr | Cl | Br | F | CH |
| Cl | c-Pr | Cl | Cl | Cl | CH | Br | t-Bu | Cl | Br | F | CH |
| Cl | c-PrCH$_2$ | Cl | Cl | Cl | CH | Br | c-Pr | Cl | Br | F | CH |
| Cl | 1-CH$_3$-c-Pr | Cl | Cl | Cl | CH | Br | c-PrCH$_2$ | Cl | Br | F | CH |
| Cl | H | Cl | Cl | Br | CH | Br | 1-CH$_3$-c-Pr | Cl | Br | F | CH |
| Cl | Me | Cl | Cl | Br | CH | Br | H | Cl | Br | Cl | CH |
| Cl | Et | Cl | Cl | Br | CH | Br | Me | Cl | Br | Cl | CH |
| Cl | i-Pr | Cl | Cl | Br | CH | Br | Et | Cl | Br | Cl | CH |
| Cl | t-Bu | Cl | Cl | Br | CH | Br | i-Pr | Cl | Br | Cl | CH |
| Cl | c-Pr | Cl | Cl | Br | CH | Br | t-Bu | Cl | Br | Cl | CH |
| Cl | c-PrCH$_2$ | Cl | Cl | Br | CH | Br | c-Pr | Cl | Br | Cl | CH |
| Cl | 1-CH$_3$-c-Pr | Cl | Cl | Br | CH | Br | c-PrCH$_2$ | Cl | Br | Cl | CH |
| Cl | H | Cl | Br | F | CH | Br | 1-CH$_3$-c-Pr | Cl | Br | Cl | CH |
| Cl | Me | Cl | Br | F | CH | Br | H | Cl | Br | Br | CH |
| Cl | Et | Cl | Br | F | CH | Br | Me | Cl | Br | Br | CH |
| Cl | i-Pr | Cl | Br | F | CH | Br | Et | Cl | Br | Br | CH |
| Cl | t-Bu | Cl | Br | F | CH | Br | i-Pr | Cl | Br | Br | CH |

TABLE 4-continued

| X | R¹ | R² | R⁴ | R⁵ | Z |
|---|----|----|----|----|---|
| Br | t-Bu | Cl | Br | Br | CH |
| Br | Me | Cl | OCH₂CF₃ | F | CH |
| Br | i-Pr | Cl | OCH₂CF₃ | F | CH |
| Br | H | Cl | OCH₂CF₃ | Cl | CH |
| Br | Et | Cl | OCH₂CF₃ | Cl | CH |
| Br | t-Bu | Cl | OCH₂CF₃ | Cl | CH |
| Br | Me | Cl | OCH₂CF₃ | Br | CH |
| Br | i-Pr | Cl | OCH₂CF₃ | Br | CH |
| Cl | H | Cl | OCHF₂ | F | CH |
| Cl | Et | Cl | OCHF₂ | F | CH |
| Cl | t-Bu | Cl | OCHF₂ | F | CH |
| Cl | Me | Cl | OCHF₂ | Cl | CH |
| Cl | i-Pr | Cl | OCHF₂ | Cl | CH |
| Cl | H | Cl | OCHF₂ | Br | CH |
| Cl | Et | Cl | OCHF₂ | Br | CH |
| Cl | t-Bu | Cl | OCHF₂ | Br | CH |
| Br | Me | Cl | OCHF₂ | F | CH |
| Br | i-Pr | Cl | OCHF₂ | F | CH |
| Br | H | Cl | OCHF₂ | Cl | CH |
| Br | Et | Cl | OCHF₂ | Cl | CH |
| Br | t-Bu | Cl | OCHF₂ | Cl | CH |
| Br | Me | Cl | OCHF₂ | Br | CH |
| Br | i-Pr | Cl | OCHF₂ | Br | CH |

R⁶ is F.

| X | R¹ | R² | R⁴ | R⁵ | Z |
|---|----|----|----|----|---|
| Cl | H | Me | CF₃ | F | N |
| Cl | Me | Cl | CF₃ | Cl | N |
| Cl | Et | Me | CF₃ | Br | N |
| Cl | i-Pr | Cl | Cl | F | N |
| Cl | t-Bu | Me | Cl | Cl | N |
| Cl | c-Pr | Cl | Cl | Br | N |
| Cl | c-PrCH₂ | Me | Br | F | N |
| Cl | 1-CH₃-c-Pr | Cl | Br | Cl | N |
| Cl | H | Me | OCH₂CF₃ | F | N |
| Cl | Me | Cl | OCH₂CF₃ | Cl | N |
| Cl | Et | Me | OCH₂CF₃ | Br | N |
| Br | i-Pr | Cl | CF₃ | F | N |
| Br | t-Bu | Me | CF₃ | Cl | N |
| Br | c-Pr | Cl | CF₃ | Br | N |
| Br | c-PrCH₂ | Me | Cl | F | N |
| Br | 1-CH₃-c-Pr | Cl | Cl | Cl | N |
| Br | H | Me | Br | Cl | N |
| Br | Me | Cl | Br | Br | N |
| Br | Et | Me | OCH₂CF₃ | F | N |
| Br | i-Pr | Cl | OCH₂CF₃ | Cl | N |
| Br | t-Bu | Me | OCH₂CF₃ | Br | N |
| Cl | H | Cl | OCHF₂ | Cl | N |
| Cl | Me | Me | OCHF₂ | Br | N |
| Br | Et | Cl | OCHF₂ | F | N |
| Br | i-Pr | Me | OCHF₂ | Cl | N |
| Br | t-Bu | Cl | OCHF₂ | Br | N |
| Cl | H | Me | CF₃ | Cl | CH |
| Cl | Me | Cl | CF₃ | Br | CH |
| Cl | Et | Me | Cl | F | CH |
| Cl | i-Pr | Cl | Cl | Cl | CH |
| Cl | t-Bu | Me | Cl | Br | CH |
| Cl | c-Pr | Cl | Br | F | CH |
| Cl | c-PrCH₂ | Me | Br | Cl | CH |
| Cl | H | Cl | OCH₂CF₃ | F | CH |
| Cl | Me | Me | OCH₂CF₃ | Cl | CH |
| Cl | Et | Cl | OCH₂CF₃ | Br | CH |
| Br | i-Pr | Me | CF₃ | F | CH |
| Br | t-Bu | Cl | Cl | F | CH |
| Br | c-Pr | Me | Cl | Cl | CH |
| Br | c-PrCH₂ | Cl | Cl | Br | CH |
| Br | 1-CH₃-c-Pr | Me | Br | F | CH |
| Br | H | Cl | Br | Br | CH |
| Br | Me | Me | OCH₂CF₃ | F | CH |
| Br | Et | Cl | OCH₂CF₃ | Cl | CH |
| Br | i-Pr | Me | OCH₂CF₃ | Br | CH |
| Cl | t-Bu | Cl | OCHF₂ | F | CH |
| Cl | H | Me | OCHF₂ | Br | CH |
| Br | Me | Cl | OCHF₂ | F | CH |
| Br | Et | Me | OCHF₂ | Cl | CH |
| Br | i-Pr | Cl | OCHF₂ | Br | CH |

R⁶ is Cl.

| X | R¹ | R² | R⁴ | R⁵ | Z |
|---|----|----|----|----|---|
| Cl | H | Me | CF₃ | F | N |
| Cl | Me | Cl | CF₃ | Cl | N |
| Cl | Et | Me | CF₃ | Br | N |
| Cl | i-Pr | Cl | Cl | F | N |
| Cl | t-Bu | Me | Cl | Cl | N |
| Cl | c-Pr | Cl | Cl | Br | N |
| Cl | c-PrCH₂ | Me | Br | F | N |
| Cl | 1-CH₃-c-Pr | Cl | Br | Cl | N |
| Cl | H | Me | OCH₂CF₃ | F | N |
| Cl | Me | Cl | OCH₂CF₃ | Cl | N |
| Cl | Et | Me | OCH₂CF₃ | Br | N |
| Br | i-Pr | Cl | CF₃ | F | N |
| Br | t-Bu | Me | CF₃ | Cl | N |
| Br | c-Pr | Cl | CF₃ | Br | N |
| Br | c-PrCH₂ | Me | Cl | F | N |
| Br | 1-CH₃-c-Pr | Cl | Cl | Cl | N |
| Br | H | Me | Br | Cl | N |
| Br | Me | Cl | Br | Br | N |
| Br | Et | Me | OCH₂CF₃ | F | N |
| Br | i-Pr | Cl | OCH₂CF₃ | Cl | N |
| Br | t-Bu | Me | OCH₂CF₃ | Br | N |
| Cl | H | Cl | OCHF₂ | Cl | N |
| Cl | Me | Me | OCHF₂ | Br | N |
| Br | Et | Cl | OCHF₂ | F | N |
| Br | i-Pr | Me | OCHF₂ | Cl | N |
| Br | t-Bu | Cl | OCHF₂ | Br | N |
| Cl | H | Me | CF₃ | Cl | CH |
| Cl | Me | Cl | CF₃ | Br | CH |
| Cl | Et | Me | Cl | F | CH |
| Cl | i-Pr | Cl | Cl | Cl | CH |
| Cl | t-Bu | Me | Cl | Br | CH |
| Cl | c-Pr | Cl | Br | F | CH |
| Cl | c-PrCH₂ | Me | Br | Cl | CH |
| Cl | H | Cl | OCH₂CF₃ | F | CH |
| Cl | Me | Me | OCH₂CF₃ | Cl | CH |
| Cl | Et | Cl | OCH₂CF₃ | Br | CH |
| Br | i-Pr | Me | CF₃ | F | CH |
| Br | t-Bu | Cl | Cl | F | CH |
| Br | c-Pr | Me | Cl | Cl | CH |
| Br | c-PrCH₂ | Cl | Cl | Br | CH |
| Br | 1-CH₃-c-Pr | Me | Br | F | CH |
| Br | H | Cl | Br | Br | CH |
| Br | Me | Me | OCH₂CF₃ | F | CH |
| Br | Et | Cl | OCH₂CF₃ | Cl | CH |
| Br | i-Pr | Me | OCH₂CF₃ | Br | CH |
| Cl | t-Bu | Cl | OCHF₂ | F | CH |
| Cl | H | Me | OCHF₂ | Br | CH |
| Br | Me | Cl | OCHF₂ | F | CH |
| Br | Et | Me | OCHF₂ | Cl | CH |
| Br | i-Pr | Cl | OCHF₂ | Br | CH |

What is claimed is:

1. A method for preparing a compound of Formula 1

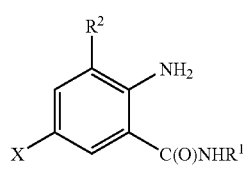

wherein R¹ is H, $C_1$-$C_4$ alkyl, cyclopropyl, cyclopropylmethyl or methylcyclopropyl;
R² is CH₃ or Cl; and
X is Cl or Br;

comprising:
  contacting a compound of Formula 2

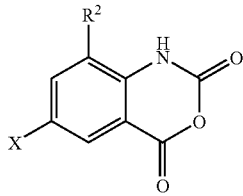

with a compound of Formula 3

R¹—NH₂                                  3 in the presence of a carboxylic acid, wherein said contact is in a substantially anhydrous reaction medium comprising a suitable organic solvent.

2. A method for preparing a compound of Formula 1

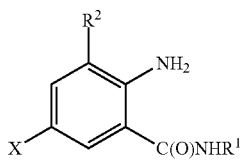

wherein R¹ is H, $C_1$-$C_4$ alkyl, cyclopropyl, cyclopropylmethyl or methylcyclopropyl;
  R² is $CH_3$ or Cl; and
  X is Cl or Br;
comprising:
  contacting a compound of Formula 2

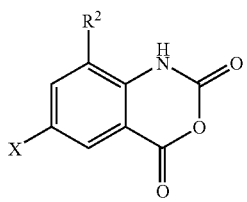

with a compound of Formula 3

R¹—NH₂                                  3 in the presence of a carboxylic acid, wherein said contact is in a reaction medium comprising ethyl acetate.

3. A method for preparing a compound of Formula 1

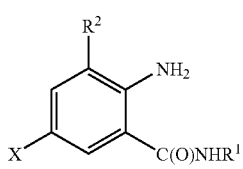

wherein R¹ is H, $C_1$-$C_4$ alkyl, cyclopropyl, cyclopropylmethyl or methylcyclopropyl;
  R² is $CH_3$ or Cl; and
  X is Cl or Br;
comprising:
  contacting a compound of Formula 2

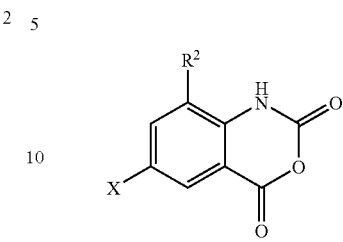

with a compound of Formula 3

R¹—NH₂                                  3 in the presence of a carboxylic acid, wherein the Compound of Formula 2 is prepared by contacting a compound of Formula 4

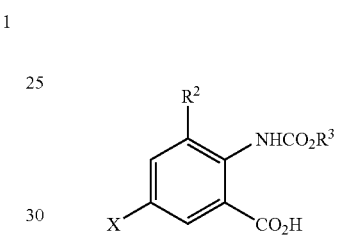

wherein R³ is $C_1$-$C_6$ alkyl or $C_3$-$C_6$ alkenyl, each optionally substituted with up to 3 halogen and up to 1 phenyl;
with phosphorus tribromide.

4. A method for preparing the compound of Formula 2

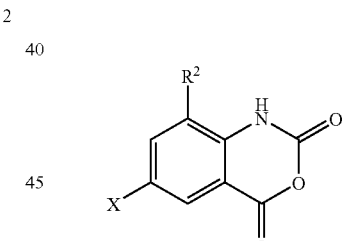

wherein R² is $CH_3$ or Cl; and X is Cl or Br; comprising:
  contacting a compound of Formula 4

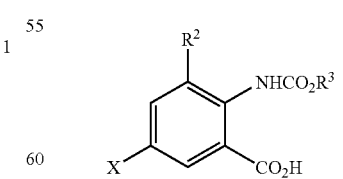

wherein R³ is $C_1$-$C_6$ alkyl or $C_3$-$C_6$ alkenyl, each optionally substituted with up to 3 halogen and up to 1 phenyl;
with phosphorus tribromide.

5. The method of claim 4 wherein R² is $CH_3$, and X is Cl.

6. A compound of Formula 4

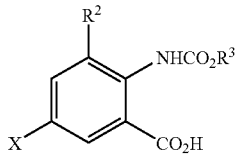

wherein $R^2$ is $CH_3$ or Cl;
$R^3$ is $C_1$-$C_6$ alkyl or $C_3$-$C_6$ alkenyl, each optionally substituted with up to 3 halogen and up to 1 phenyl; and
X is Cl or Br;
provided that when $R^2$ and X are each Cl, then $R^3$ is other than $CH_3$.

7. A compound of claim 6 wherein $R^2$ is $CH_3$ and X is Cl.
8. A compound of claim 7 wherein $R^3$ is $C_1$-$C_2$ alkyl.
9. A compound of claim 6 wherein $R^2$ is $CH_3$ and X is Br.
10. A compound of claim 9 wherein $R^3$ is $C_1$-$C_2$ alkyl.

* * * * *